United States Patent [19]  [11] 4,239,762
Krämer et al.  [45] Dec. 16, 1980

[54] COMBATING INSECTS WITH SUBSTITUTED 5-PHENYLCARBAMOYL-BARBITURIC ACIDS

[75] Inventors: Wolfgang Krämer, Wuppertal; Erich Klauke, Odenthal; Peter Roessler, Bergisch-Gladbach, all of Fed. Rep. of Germany

[73] Assignee: Bayer Aktiengesellschaft, Leverkusen, Fed. Rep. of Germany

[21] Appl. No.: 55,572

[22] Filed: Jul. 9, 1979

[30] Foreign Application Priority Data

Jul. 26, 1978 [DE] Fed. Rep. of Germany ....... 2832698

[51] Int. Cl.³ .................. A01N 43/54; C07D 239/62
[52] U.S. Cl. ................................ 424/254; 544/300; 544/301
[58] Field of Search ................. 544/301, 300; 424/254

[56] References Cited
U.S. PATENT DOCUMENTS 3,828,043  8/1974  Kay et al. ........................... 424/254
3,961,061  6/1976  Kramer et al. ..................... 544/301

OTHER PUBLICATIONS

Beriger, Chemical Abstracts, 88:62412m (1978).
Makizawa et al., Chemical Abstracts, 86:134902e (1977).

Primary Examiner—Paul M. Coughlan, Jr.
Attorney, Agent, or Firm—Sprung, Felfe, Horn, Lynch & Kramer

[57] ABSTRACT

Substituted 5-phenylcarbamoyl-barbituric acids of the formula

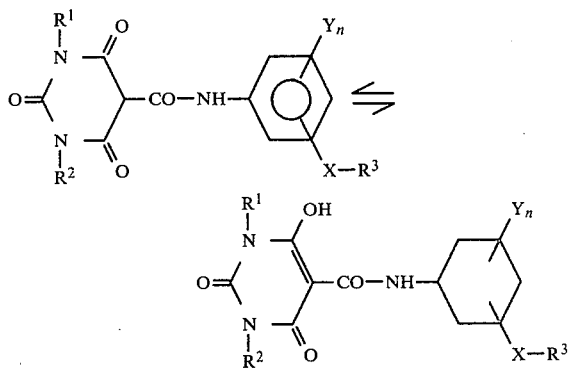

in which
R¹ represents hydrogen or alkyl,
R² represents hydrogen or alkyl,
R³ represents halogenoalkyl, or phenyl substituted by halogenoalkyl,
X represents oxygen or sulphur,
Y represents halogen or halogenoalkyl, and
n represents 0, 1 or 2, or
X—R³ and Y in the ortho-position to one another conjointly may alternatively represent the —O—CF₂—O—CF₂— group, or salts thereof with a physiologically tolerated base, which possess insecticidal properties.

9 Claims, No Drawings

COMBATING INSECTS WITH SUBSTITUTED 5-PHENYLCARBAMOYL-BARBITURIC ACIDS

The present invention relates to and has for its object the provision of particular new 5-substituted-phenylcarbamoyl-barbituric acids and salts thereof which possess insecticidal properties, active compositions in the form of mixtures of such compounds with solid and liquid dispersible carrier vehicles, and methods for producing such compounds and for using such compounds in a new way expecially for combating pests, e.g. insects, with other and further objects becoming apparent from a study of the within specification and accompanying examples.

It has already been disclosed that certain 1,3-dialkyl-5-alkyl- and -phenyl-carbamoyl-barbituric acid derivatives can be employed for combating insects (see Japanese Pat. No. J5 1123-823[=Derwent 93 363X/50] and Belgian Pat. No. 854,287). Their action is, however, not always entirely satisfactory, especially when they are used as inhibitors of the development of insects.

The present invention now provides, as new compounds, the substituted 5-phenylcarbamoyl-barbituric acids of the general formula

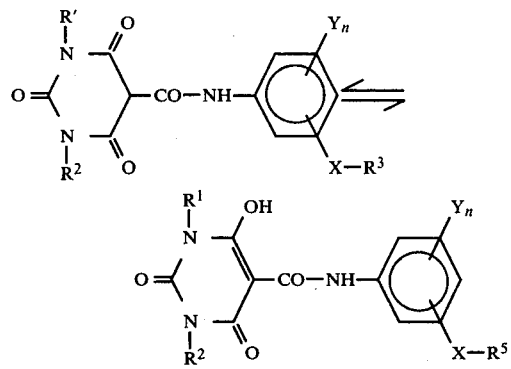

in which
R$^1$ represents hydrogen or alkyl,
R$^2$ represents hydrogen or alkyl,
R$^3$ represents halogenoalkyl, or phenyl substituted by halogenoalkyl,
X represents oxygen or sulphur,
Y represents halogen or halogenoalkyl, and
n represents 0, 1 or 2, or
X—R$^3$ and Y in the ortho-position to one another conjointly may alternatively represent the —O—CF$_2$—O—CF$_2$-group,
and their salts with physiologically tolerated bases.

Surprisingly, the substituted 5-phenylcarbamoyl-barbituric acids according to the invention exhibit a greater insect development-inhibiting action than the 1,3-dialkyl-5-alkyl- and -phenyl-carbamoyl-barbituric acid derivatives known from the prior art, which are the nearest compounds chemically and in respect of their action. The active compounds according to the invention thus represent an enrichment of the art.

Preferably, in formula (I), R$^1$ and R$^2$, which may be identical or different, each represent hydrogen or alkyl with 1 to 4 carbon atoms, R$^3$ represents halogenoalkyl with up to 2 carbon atoms and with up to 5 identical or different halogen atoms (especially fluorine and/or chlorine atoms) or represents phenyl which is substituted by halogenoalkyl with up to 2 carbon atoms and up to 5 identical or different halogen atoms (especially fluorine and/or chlorine atoms), X represents oxygen and sulphur, Y represents fluorine, chlorine, bromine or halogenoalkyl with up to 2 carbon atoms and up to 5 identical or different halogen atoms (especially fluorine and/or chlorine atoms), and n represents 0, 1 or 2, or —X—R$^3$ and Y in the ortho-position to one another conjointly represent the group —O'CF$_2$—O—CF$_2$—.

Particularly preferred compounds of the formula (I) are those in which R$^1$ and R$^2$ represent hydrogen, methyl, ethyl or isopropyl, R$^3$ represents trifluoromethyl, 1,1,2-trifluoro-2-chloro-ethyl, 1,1,2,2-tetrafluoroethyl, 1,1,2,2-tetrafluoro-2-chloroethyl, chlorodifluoro-methyl, dichlorofluoromethyl, trichloromethyl or trifluoromethylphenyl, X represents oxygen or sulphur, Y represents fluorine, chlorine or trifluoromethyl, and n represents 0, 1 or 2, or —X—R$^3$ and Y, in the ortho-position to one another, conjointly represent the group —O—CF$_2$—O—CF$_2$—.

In addition to the compounds mentioned in the preparative examples, the following compounds of the general formula (I) may be mentioned:

| R$^1$ | R$^2$ | —X—R$^3$ | Y$_n$ |
|---|---|---|---|
| CH$_3$ | C$_2$H$_5$ | 4-O—CF$_3$ | 3-Cl |
| CH$_3$ | C$_2$H$_5$ | 4-S—CF$_3$ | 3-Cl |
| CH$_3$ | CH$_3$ | 4-S—CF$_3$ | 3-Cl |
| C$_2$H$_5$ | C$_2$H$_5$ | 4-S—CF$_3$ | 3-Cl |
| CH$_3$ | C$_2$H$_5$ | 4-OCF$_3$ | 2-Cl |
| CH$_3$ | CH$_3$ | 4-OCF$_3$ | 2-Cl |
| C$_2$H$_5$ | C$_2$H$_5$ | 4-OCF$_3$ | 2-Cl |
| CH$_3$ | C$_2$H$_5$ | 4-O—CF$_2$—CHClF | 3-Cl |
| CH$_3$ | CH$_3$ | 4-O—CF$_2$—CHClF | 3-Cl |
| C$_2$H$_5$ | C$_2$H$_5$ | 4-O—CF$_2$—CHClF | 3-Cl |
| CH$_3$ | C$_2$H$_5$ | 4-O—CF$_3$ | — |
| CH$_3$ | CH$_3$ | 4-O—CF$_3$ | — |
| C$_2$H$_5$ | C$_2$H$_5$ | 4-O—CF$_3$ | — |
| CH$_3$ | C$_2$H$_5$ | 4-O—CF$_2$—CHF$_2$ | — |
| CH$_3$ | CH$_3$ | 4-O—CF$_2$—CHF$_2$ | — |
| C$_2$H$_5$ | C$_2$H$_5$ | 4-O—CF$_2$—CHF$_2$ | — |
| CH$_3$ | C$_2$H$_5$ | 3-O—CF$_2$—CHClF | — |
| CH$_3$ | CH$_3$ | 3-O—CF$_2$—CHClF | — |
| C$_2$H$_5$ | C$_2$H$_5$ | 3-O—CF$_2$—CHClF | — |
| CH$_3$ | C$_2$H$_5$ | 4-O—CF$_2$—CF$_2$Cl | 3-Cl |
| CH$_3$ | CH$_3$ | 4-O—CF$_2$—CF$_2$Cl | 3-Cl |
| C$_2$H$_5$ | C$_2$H$_5$ | 4-O—CF$_2$—CF$_2$Cl | 3-Cl |
| CH$_3$ | C$_2$H$_5$ | 4-S—CF$_2$Cl | 3-Cl |
| CH$_3$ | CH$_3$ | 4-S—CF$_2$Cl | 3-Cl |
| C$_2$H$_5$ | C$_2$H$_5$ | 4-S—CH$_2$Cl | 3-Cl |
| CH$_3$ | C$_2$H$_5$ | 4-S—CF$_3$ | — |
| CH$_3$ | CH$_3$ | 4-S—CF$_3$ | — |
| C$_2$H$_5$ | C$_2$H$_5$ | 4-S—CF$_3$ | — |
| CH$_3$ | C$_2$H$_5$ | 4-O—⟨phenyl-CF$_3$⟩ | — |
| CH$_3$ | CH$_3$ | 4-O—⟨phenyl-CF$_3$⟩ | — |
| C$_2$H$_5$ | C$_2$H$_5$ | 4-O—⟨phenyl-CF$_3$⟩ | — |

-continued

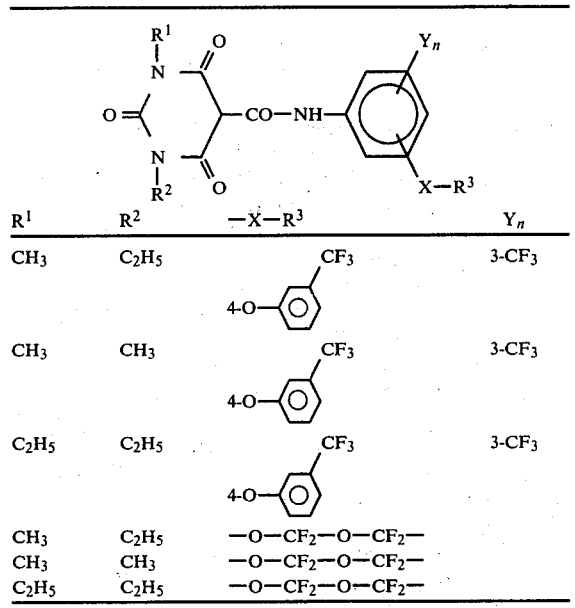

| R¹ | R² | —X—R³ | Yₙ |
|---|---|---|---|
| CH₃ | C₂H₅ | 4-O-C₆H₄-CF₃ | 3-CF₃ |
| CH₃ | CH₃ | 4-O-C₆H₄-CF₃ | 3-CF₃ |
| C₂H₅ | C₂H₅ | 4-O-C₆H₄-CF₃ | 3-CF₃ |
| CH₃ | C₂H₅ | —O—CF₂—O—CF₂— | |
| CH₃ | CH₃ | —O—CF₂—O—CF₂— | |
| C₂H₅ | C₂H₅ | —O—CF₂—O—CF₂— | |

The invention also provides a process for the preparation of a substituted 5-phenylcarbamoyl-barbituric acid of the formula (I) in which a barbituric acid of the general formula

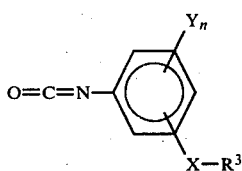

(II), in which
R¹ and R² have the abovementioned meanings, is reacted with an isocyanate of the general formula (III),

O=C=N—C₆H₃(Yₙ)(X—R³)

in which
R³, X, Y and n have the abovementioned meanings, in the presence of a catalyst and optionally in the presence of a diluent.

Furthermore, the substituted 5-phenylcarbamoyl-barbituric acids of the formula (I), obtainable according to the invention, can be converted to the salts by reaction with bases.

If, for example, 1,2-dimethyl-barbituric acid and 3-chloro-4-trifluoromethoxy-phenyl isocyanate are used as starting materials, the course of the reaction can be represented by the following equation:

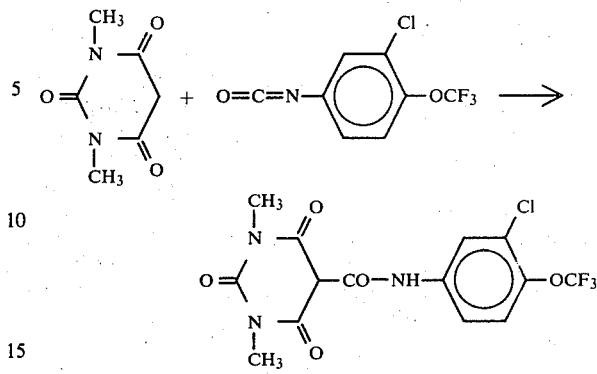

The formula (II) provides a general definition of the barbituric acids to be used as starting materials for the process according to the invention. In this formula, R¹ and R² preferably have the meanings which have already been mentioned as preferred in the description of the compounds of the formula (I).

The barbituric acids of the formula (II) are generally known compounds of organic chemistry. The following may be mentioned as examples: 1,3-dimethyl-barbituric acid, 1-methyl-barbituric acid, 1-ethyl-3-methyl-barbituric acid, 1,3-diethylbarbituric acid, 1-ethylbarbituric acid, 1-methyl-3-isopropyl-barbituric acid, 1-methyl-3-propyl-barbituric acid, 1-methyl-3-butyl-barbituric acid, 1-methyl-3-isobutyl-barbituric acid, 1-methyl-3-sec.-butyl-barbituric acid, 1-methyl-3-tert.-butyl-barbituric acid and barbituric acid.

The formula (III) provides a general definition of the isocyanates also to be used as starting materials for the process according to the invention. In this formula, R³, X, Y and n preferably have the meanings which have already been mentioned as preferred in the description of the compounds of the formula (I).

Isocyanates of the formula (III) are known and can be prepared in accordance with generally customary and known processes, for example by reaction of amines with phosgene, followed by heating. These processes are known for general textbooks on organic chemistry. The following may be mentioned as examples: 4-trifluoromethoxyphenyl isocyanate, 4-trifluoromethylthiophenyl isocyanate, 2-chloro-4-trifluoromethoxyphenyl isocyanate, 3-chloro-4-trifluoromethoxyphenyl isocyanate, 2-chloro-4-trifluoromethylthiophenyl isocyanate, 3-chloro-4-trifluoromethylthiophenyl isocyanate, 4-chlorodifluoromethoxyphenyl isocyanate, 4-chlorodifluoromethylthiophenyl isocyanate, 2-chloro-4-chlorodifluoromethoxyphenyl isocyanate, 3-chloro-4-chlorodifluoromethoxyphenyl isocyanate, 2-chloro-4-chlorodifluoromethylthiophenyl isocyanate, 3-chloro-4-chlorodifluoromethylthiophenyl isocyanate, 2-chloro-4-chlorodifluoromethylthiophenyl isocyanate, 3-chloro-4-chlorodifluoromethylthiophenyl isocyanate, 4-(1,1,2,2-tetrafluoroethoxy)-phenyl isocyanate 3-chloro-4-(1,1,2,2-tetrafluoroethoxy)-phenyl isocyanate, 2-chloro-4-(1,1,2,2-tetrafluoroethoxy)-phenyl isocyanate, 4-(1,1,2-trifluoro-2-chloro-ethoxy)-phenyl (thio)-isocyanate, 3-chloro-4-(1,1,2-trifluoro-2-chloro-ethoxy)-phenyl isocyanate, 3-(1,1,2-trifluoro-2-chloro-ethoxy)-phenyl isocyanate, 4-(1,1,2,2-tetrafluoro-2-chloro-ethoxy)-phenyl isocyanate, 3-chloro-4-(1,1,2,2-tetrafluoro-2-chloro-ethoxy)-phenyl isocyanate, 2-chloro-4-(1,1,2,2-tetrafluoro-2-chloro-ethoxy)-phenyl isocyanate, 4-(3'-trifluoromethylphenoxy)-phenyl isocyanate, 3-trifluoromethyl-4-(3'-trifluoromethylphenoxy)-phenyl isocyanate and 2,2,4,4-tetrafluoro-1,3-benzodioxan-6-yl isocyanate.

All physiologically tolerated bases are suitable for the preparation of salts of the compounds of the formula (I). Sodium salts, potassium salts and, in particular, ammonium salts and trialkylamine salts, for example triethylamine salts, may be mentioned as preferences.

All inert organic solvents are suitable as diluents for carrying out the process according to the invention, especially ether, such as diethyl ether, tetrahydrofuran or dioxane; ketones, such as acetone and methyl ethyl ketone; aliphatic and aromatic hydrocarbons, such as ligroin, petroleum ether, benzene, toluene or xylene; and chlorinated hydrocarbons, such as carbon tetrachloride, chloroform and methylene chloride.

All basic catalysts which can usually be employed may be used as catalysts in carrying out the process according to the invention. These include, as preferences, organic bases, such as triethylamine or pyridine, and tin-organic compounds, such as dibutyl-tin dilaurate.

In carrying out the process according to the invention, the reaction temperatures can be varied within a substantial range. In general, the reaction is carried out at from 0° to 150° C., preferably from 20° to 100° C.

In carrying out the process according to the invention, preferably 1 mole of isocyanate of the formula (III) and 0.1-1 mole of catalyst are employed per mole of barbituric acid of the formula (II). To isolate the resultant compound of the formula (I), the reaction mixture is acidified and concentrated in vacuo, water is added to the residue and the product is filtered off, washed thoroughly with alcohol and dried.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Buphalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nibilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dascus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,*

Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol esters, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

When used at fairly high concentrations, the active compounds according to the invention also exhibit fungicidal actions.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects and acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative example:

EXAMPLE 1

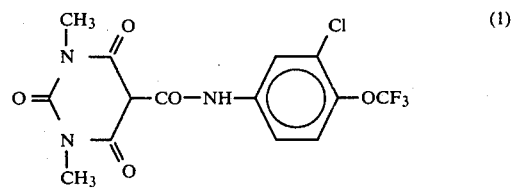

7.8 g (0.05 mol) of 1,3-dimethylbarbituric acid were suspended in 150 ml of dioxane and 5 g (0.05 mol) of triethylamine, and 11.85 g (0.05 mol) of 3-chloro-4-trifluoromethoxy-phenyl isocyanate were added. The mixture was stirred for 5 hours under reflux. When it had cooled, the reaction mixture was brought to a pH value of 3 with 2 N hydrochloric acid and was concentrated in vacuo by distilling off the solvent. The residue was mixed with 200 ml of water, filtered off, mixed with 100 ml of isopropanol, again filtered off and dried. 16.5 g (74% of theory) of 5-(3'-chloro-4'-trifluoromethoxyphenyl-carbamoyl)-1,3-dimethyl-barbituric acid, of melting point 160° C., were obtained.

The compounds of the following table were obtained analogously:

TABLE 1

[Structure: barbituric acid derivative with R¹, R² on nitrogens, CO—NH—phenyl ring substituted with $Y_n$ and $X-R^3$]

| Example No. | $R^1$ | $R^2$ | $-XR^3$ | $Y_n$ | Melting point (°C.) |
|---|---|---|---|---|---|
| 2 | $C_2H_5$ | $C_2H_5$ | 4-$OCF_3$ | 3-Cl | 134–35 |
| 3 | $C_2H_5$ | $CH_3$ | 4-$OCF_3$ | 2-Cl | 119 |
| 4 | $C_2H_5$ | $CH_3$ | 4-$OCF_2CHClF$ | 3-Cl | 124 |
| 5 | $C_2H_5$ | $CH_3$ | 4-$OCF_2CF_2H$ | H | 119 |
| 6 | $C_2H_5$ | $CH_3$ | 4-$OCF_3$ | H | 118–20 |
| 7 | $C_2H_5$ | $CH_3$ | 4-$OCF_3$ | 3-Cl | 130–2 |
| 8 | $C_2H_5$ | $CH_3$ | 3-$OCF_2CHClF$ | H | 98–99 |
| 9 | $C_2H_5$ | $CH_3$ | 4-$SCF_2Cl$ | 3-Cl | 138–40 |
| 10 | $C_2H_5$ | $CH_3$ | 4-$SCF_3$ | H | 142 |
| 11 | $C_2H_5$ | $CH_3$ | 4-O, 3-$F_2C$—$CF_2$—O (cyclic) | | 98–100 |
| 12 | $C_2H_5$ | $CH_3$ | 4-O-phenyl-$CF_3$ | H | 172–80 |
| 13 | $C_2H_5$ | $CH_3$ | 4-O-phenyl-$CF_3$ | 3$CF_3$ | 63–70 |

The activity of the compounds of this invention is illustrated by the following examples wherein the compounds according to the present invention are each identified by the number (given) in brackets) from Example 1 and the table hereinabove.

Moreover, in these examples, which relate to the development-inhibiting action of the active compounds, the morphological changes, such as half-pupated insects, incompletely slipped larvae or caterpillars, defective wings, pupal cuticula in the case of imagos and the like, over the entire stated development of the test insects, were regarded as malformations. The sum of the morphological malformations, together with the insects killed during shedding or metamorphosis, was determined as a percentage of the total number of test insects employed.

EXAMPLE 2

Development-inhibiting action/ingestion test

| | |
|---|---|
| Test insects: | *Plutella maculipennis* (caterpillars in the 4th stage of development) |
| Number of test insects: | 20 specimens |
| Test insects: | *Phaedon cochleariae* (larvae in the 4th stage of development) |
| Number of test insects: | 20 specimens |
| Feed plants: | Cabbage plants (*Brassica olearacea*) |
| Solvent: | 10 parts by weight of acetone |
| Emulsifier: | 1 part by weight of alkylaryl polyglycol ether |

To produce a suitable preparation of active compound, 2 parts by weight of active compound were mixed with the stated amount of solvent and emulsifier and with sufficient water to give a 1% strength mixture, which was diluted with water to the desired concentration.

The test insects were fed with leaves of the feed plants, which were provided with a uniform spray covering of the active compound preparation in such a way that the desired concentration of active compound (amount of active compound per unit surface area) was obtained on the leaves, until the imago develped.

As a control, leaves coated only with a solvent- and emulsifier-water mixture of the corresponding concentration were used as the feed.

In this test, for example, the following compounds showed a superior action compared to the prior art: (1) and (2).

EXAMPLE 3

Development-inhibiting action/Laphygma caterpillar test

| | |
|---|---|
| Test insects | *Laphygma frugiperda* (caterpillars) |
| Feed: | 1 cm thick disc of 3 cm diameter, of an air-dried artificial feed based on shredded beans, yeast, vitamin mixture, leaf poweder, agar and preservative |
| Solvent: | 10 parts by weight of acetone |
| Emulsifier: | 1 part by weight of alkylaryl polyglycol ether |

To produce a suitable preparation of active compound, 2 parts by weight of active compound were mixed with the stated amount of solvent and emulsifier and with sufficient water to give a 1% strength mixture, which was diluted with water to the desired concentration.

Each test insect was placed on a separate feed disc moistened with 1.5 ml of active compound preparation of the desired concentration, and was observed until the imago slipped.

As a control, test insects were each placed on a separate feed disc moistened with 1.5 ml of a solvent, emulsifier and water mixture of the corresponding concentration and observed until the imago slipped.

In this test, for example, the compound 1 showed a superior action compared to the prior art.

It will be understood that the foregoing specification and examples are set forth by way of illustration and not limitation, and that various modifications and changes may be made without departing from the spirit and scope of the present invention.

What we claim is:

1. A 5-substituted-phenyl carbamoyl-barbituric acid of the formula

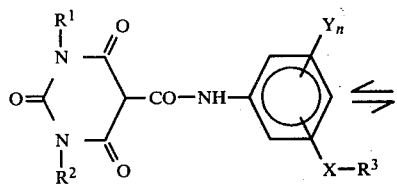

in which
- $R^1$ represents hydrogen or alkyl with 1 to 4 carbon atoms,
- $R^2$ represents hydrogen or alkyl with 1 to 4 carbon atoms,
- $R^3$ represents halogenoalkyl with up to 2 carbon atoms and up to 5 halogen atoms, or phenyl substituted by halogenoalkyl with up to 2 carbon atoms and up to 5 halogen atoms,
- X represents oxygen or sulphur,
- Y represents halogen or halogenoalkyl with up to 2 carbon atoms and up to 5 halogen atoms, and
- n represents 0, 1 or 2, or
- $X-R^3$ and Y in the ortho-position to one another conjointly may alternatively represent the $-O-CF_2-O-CF_2$-group, or a salt thereof with a physiologically tolerated base.

2. A compound or salt thereof according to claim 1, wherein such compound is 5-(3'-chloro-4'trifluoromethoxy-phenyl-carbamoyl)-1,3-dimethyl-barbituric acid of the formula

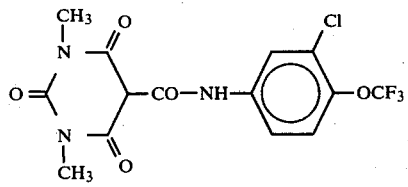

3. A compound or salt thereof according to claim 1, wherein such compound is 5-(3'-chloro-4'-trifluoromethoxy-phenyl-carbamoyl)-1,3-diethyl-barbituric acid of the formula

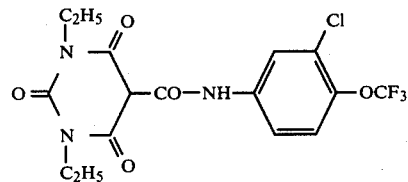

4. A compound or salt thereof according to claim 1, wherein such compound is 5-(2'-chloro-4'-trifluoromethoxy-phenyl-carbamoyl)-1-methyl-3-ethyl-barbituric acid of the formula

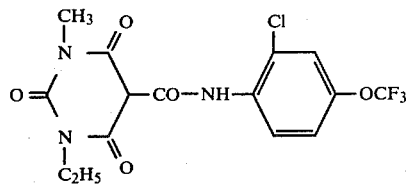

5. A compound or salt thereof according to claim 1, wherein such compound is 5-[3'-chloro-4'-(2''-chloro-1'',1'',2''-trifluoroethoxy)-phenyl-carbamoyl]-1-methyl-3-ethyl-barbituric acid of the formula

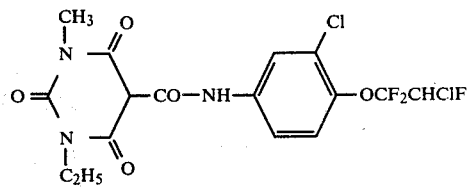

6. A compound or salt thereof according to claim 1, wherein such compound is 5-(2,2,4,4-tetrafluor-1,3-benzodioxin-6-yl-carbamoyl)-1-methyl-3-ethyl-barbituric acid of the formula

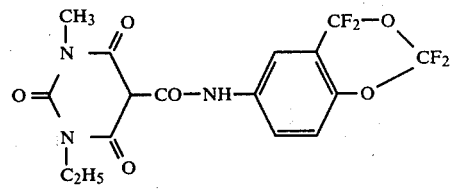

7. An arthropodicidal composition containing as active ingredient an arthropodicidally effective amount of a compound or salt according to claim 1 in admixture with a diluent.

8. A method of combating arthropods which comprises applying to the arthropods, or to a habitat thereof, an arthropodicidally effective amount of a compound or salt according to claim 1.

9. The method according to claim 8, in which said compound is 5-(3'-chloro-4'-trifluoromethoxy-phenyl-carbamoyl)-1,3-dimethyl-barbituric acid, 5-(3'-chloro-4'-trifluoromethoxy-phenyl-carbamoyl)-1,3-diethyl-barbituric acid, 5-(2'-chloro-4-trifluoromethoxy-phenyl-carbamoyl)-1-methyl-3-ethyl-barbituric acid, 5-[3'-chloro-4'-(2''-chloro-1'',1'',2''-trifluoroethoxy)-phenyl-carbamoyl]-1-methyl-3-ethyl-barbituric acid, 5-(3',4'-difluoromethylenoxy-phenyl-carbamoyl)-1-methyl-3-ethyl-barbituric acid, or a salt thereof.

* * * * *